United States Patent

Choi et al.

[11] Patent Number: 5,849,772
[45] Date of Patent: Dec. 15, 1998

[54] CARBAMATE COMPOUNDS AND PROCESSES FOR PREPARING THE SAME

[75] Inventors: Yong Moon Choi, Towaco, N.J.; Dong Il Han, Taejon, Rep. of Korea; Kwang Hyouk Lee, Taejon, Rep. of Korea; Hyung Cheol Kim, Taejon, Rep. of Korea

[73] Assignee: Yukong Limited, Seoul, Rep. of Korea

[21] Appl. No.: 612,903

[22] PCT Filed: Sep. 21, 1995

[86] PCT No.: PCT/KR95/00124

§ 371 Date: Jun. 17, 1996

§ 102(e) Date: Jun. 17, 1996

[87] PCT Pub. No.: WO96/09283

PCT Pub. Date: Mar. 28, 1996

[30] Foreign Application Priority Data

Sep. 22, 1994 [KR] Rep. of Korea .................. 1994-23910
Sep. 22, 1994 [KR] Rep. of Korea .................. 1994-23911
Sep. 22, 1994 [KR] Rep. of Korea .................. 1994-23912

[51] Int. Cl.⁶ ..................... C07D 213/30; C07D 271/08; A61K 31/44; A61K 31/165
[52] U.S. Cl. .......................... 514/357; 514/538; 546/335; 560/157
[58] Field of Search ............................ 546/335; 560/157; 514/357, 538

[56] References Cited

U.S. PATENT DOCUMENTS

| | | | |
|---|---|---|---|
| 2,884,444 | 4/1959 | Berger et al. ............................ | 560/157 |
| 2,937,119 | 5/1960 | Berger et al. ............................ | 560/157 |
| 3,265,728 | 8/1966 | Bossinger ................................ | 260/482 |
| 4,221,582 | 9/1980 | Garrod et al. ........................... | 544/158 |

OTHER PUBLICATIONS

Chemical Abstracts, vol. 119, No. 21, Abstract 216, 700b, Nov. 22, 1993, p. 14 (Advsomalle et al.).
Choi et al, J. of Org. Chem, vol. 57, No. 21, 1992 pp. 5764–5766.
Ludwig et al, J. of Med. Chem, vol. 12, No. 3, 1969, pp. 462–472.
Ludwig et al., J.A.C.S., 73, 5799 (1951).
Berger, J. Pharm. Exp. Ther., 104, 229 (1952).

*Primary Examiner*—Zinna Northington Davis
*Attorney, Agent, or Firm*—Abelman, Frayne & Schwab

[57] ABSTRACT

(S)-2-Aryl-1,3-propanediol monocarbamate and its intermediate, (S)-3-acetoxy-2-aryl-propanol carbamate, represented by the following formulas I and II, respectively, have pharmaceutically useful activity against for central nervous system disorders including nervous myalgia, epilepsy and cerebral apoplexy:

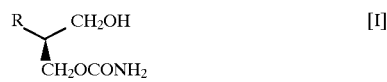

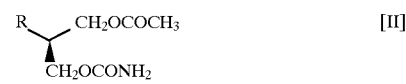

wherein, R is

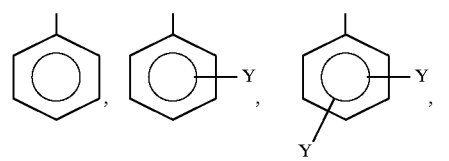

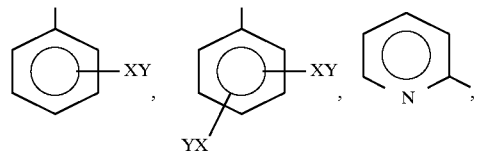

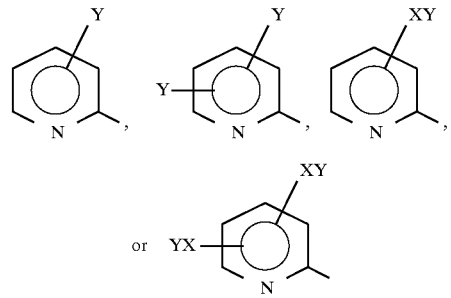

wherein X is an oxygen atom or a sulfur atom; and Y represents a halogen element, trifluoromethyl, or a lower alkyl group containing one to three carbon atoms.

14 Claims, No Drawings

CARBAMATE COMPOUNDS AND PROCESSES FOR PREPARING THE SAME

This application is a 371 of PCT/KR95/00124 Sep. 21, 1995.

BACKGROUND OF THE INVENTION

1. Field of the Invention

The present invention relates, in general, to novel enantiomeric carbamate compounds pharmaceutically useful for central nervous disorders and, more particularly, to (S)-2-aryl-1,3-propanediol monocarbamate derived from (R)-3-acetoxy-2-arylpropanol carbamate and to (S)-3-acetoxy-2-arylpropanol carbamate, its intermediate. Also, the present invention is concerned with processes for preparing the novel carbamate compounds.

2. Description of the Prior Art

Carbamates have been effectively used for controlling central nervous system (hereinafter referred to as "CNS") disorders, especially, as an antiepiletic and a centrally acting muscle relaxant. For example, 2-methyl-2-propyl-1,3-propanediol dicarbamate was reported in J. Am. Chem. Soc., 73, 5779 (1951), and the pharmaceutical activity thereof was ascertained in J. Pharmacol. Exp. Ther., 104, 229 (1952).

U.S. Pat. No. 3,256,728 discloses that the compounds, represented by the following general formula A, are pharmaceutically useful therapeutics for CNS disorders:

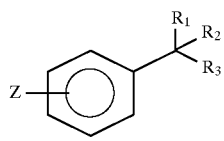

[A]

wherein, $R_1$ is a carbamate or methylene carbamate; $R_2$ is an alkyl group containing one or two carbon atoms, a hydroxy alkyl group containing one or two carbon atoms, hydroxy or hydrogen; $R_3$ is hydrogen or an alkyl group containing one or two carbon atoms; and Z represents a halogen such as fluorine, chlorine, bromine or iodine, a methylmethoxy group, a phenyl group, a nitro group or an amine group.

Besides, other carbamate compounds which are very useful therapeutic medicines against CNS disorders, in particular, as antiepiletic and centrally acting muscle relaxant, are disclosed, including 2-phenyl-1,3-propanediol dicarbamate in U.S. Pat. No. 2,884,444 and isopropyl meprobamate in U.S. Pat. No. 2,937,119. At present, various researches for such carbamate compounds are being actively continued in the art.

SUMMARY OF THE INVENTION

Based on intensive and thorough study and research by the present inventors, it was found that the carbamate compounds represented by the following structural formulas I and II are useful for the treatment and prevention of CNS diseases including nervous myalgia, epilepsy and cerebral apoplexy:

[I]

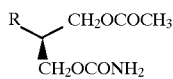

[II]

wherein, R is

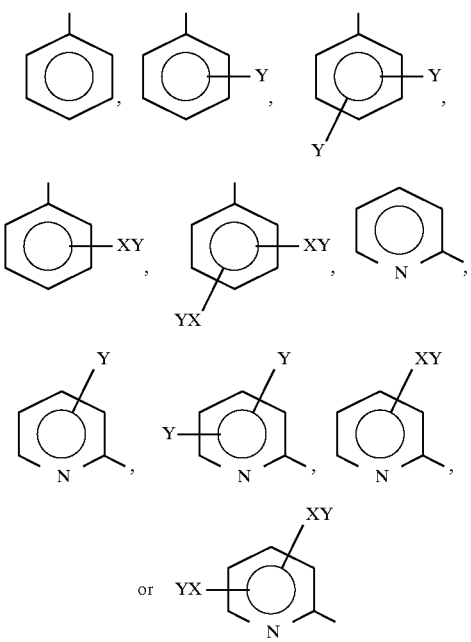

wherein X is an oxygen atom or a sulfur atom; and Y represents a halogen element, trifluoromethyl, or a lower alkyl group containing one to three carbon atoms.

In addition, taking advantage of the far superior activity of single enantiomeric isomer to racemic mixture in biological systems, the present inventors developed the enantiomers of Formulas I and II, which had never been found, and applied them as pharmaceutically active ingredients against CNS diseases.

The carbamate compounds of Formulas I and II are chiral molecules with a chiral center of carbon at 2-propyl and may have either an (S) or (R)-configuration.

Accordingly, it is an object of the present invention to provide novel (S)-enantiomeric compounds represented by Formulas I and II, which have pharmaceutically useful activity against central nervous system diseases.

It is another object of the present invention to provide a method for preparing the compounds of Formulas I and II at high yield and high purity within a short time.

DETAILED DESCRIPTION OF THE INVENTION

The compound of Formula II can be prepared by treating (R)-3-acetoxy-2-aryl-propanol, represented by the following formula III:

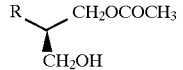

[III]

wherein, R is as defined above, with phosgene in a mixture of aromatic hydrocarbon and halogenohydrocarbon in the presence of amine base, and followed by anhydrous ammonia.

Available aromatic hydrocarbons include benzene, toluene and xylene and a halogenohydrocarbon is selected from the group consisting of chloroform, dicholomethane, 1,2-dichloroethane and trichloroethane. The preferred solvent is a mixture of toluene and dichloromethane.

As the amine base, antipyrine, diisopropylethylamine, diethylamine, triethylamine or pyridine is available, with a preference to such a sterically hindered base as triethylamine, diisopropylethylamine or antipyrine.

Temperature is maintained at −30° to 0° C. upon reaction with phosgene while the reaction with anhydrous ammonia is carried out at a temperature of −70° to 0° C.

For use, anhydrous ammonia is condensed to a liquid. It is added at an excess of 10 to 100 equivalents and preferably at an excess of 25 to 50 equivalents.

In accordance with the present invention, the compound of Formula I can be converted from (S)-3-acetoxy-2-aryl-propanol carbamate, represented by Formula II, through the catalytic reaction of hydrolase in a buffer solution. High yield and optical purity can be accomplished within a short time by the enzymatic hydrolysis of (S)-3-acetoxy-2-aryl-propanol carbamate into (S)-2-aryl-1,3-propanediol monocarbamate.

Generally, enzymes show a far higher catalytic activity than chemical catalysts while giving less by-products. In addition, since the enzymatic conversion of (S)-3-acetoxy-2-arylpropanol carbamate into (S)-2-aryl-1,3-propanediol monocarbamate is carried out at a low temperature in a neutral aqueous solution, for example, phosphate buffer solution, the side-reactions attributable to the enzyme can be eliminated. Following the hydrolysis, the enzyme used can be almost completely removed only by filtration without lowering the product yield. Accordingly, the present invention is very advantageous in time and cost.

In more detail, the (S)-3-acetoxy-2-arylpropanol carbamate of Formula II is dissolved in a phosphate buffer solution and then, vigorously stirred at a temperature of 0° to 35° C. and with ordinary pressure in the presence of hydrolase. Preference is given to a temperature of 10° to 25° C. Care must be taken to control the reaction temperature. A reaction temperature of higher than 35° C. makes the hydrolysis proceed faster but causes the enzyme to be lowered in selectivity, deleteriously affecting the optical purity of the product.

The phosphate buffer solution has a pH ranging from 6 to 9 with a preference of 7. For example, if the phosphate buffer solution has a pH of higher or lower than 7, the optical purity of the product becomes poor. In order for the selectivity of the enzyme not to be lowered, the phosphate buffer solution is preferably diluted into 0.01 to 0.1 mole solution.

With regard to the hydrolase used for the conversion, various sources are available. Representative examples include lipase extracted from pig's pancreas (PPL), Candida lipase (CCL), Aspagillus lipase (ANL), Pseudomonas lipase (PSL) and an esterase from pig's liver (PLE), with a preference for PLE.

Usually at 4 to 5 hours after adding the enzyme, the conversion reaction of (S)-3-acetoxy-2-aryl-propanol carbamate into (S)-2-aryl-1,3-propanediol monocarbamate is terminated. Thin layer chromatography or high performance liquid chromatography may be used to determine the termination point of the conversion reaction.

From the resultant reaction mixture, the enzyme may be filtered off simply and then, the solvent is removed by using a rotary evaporator. Purification by column chromatography gives (S)-2-aryl-1,3-propanediol monocarbamate of Formula I, a novel compound.

Likewise, (R)-3-acetoxy-2-aryl-propanol of Formula III can be prepared by use of an enzyme. For this, PPL, CCL or PSL is immobilized to cellite. Preference is given to PPL and PSL. 2-aryl-1,3-propanediol is dissolved in anhydrous alkyl acetate, such as methyl acetate, ethyl acetate, propyl acetate and vinyl acetate, or anhydrous alkenyl acetate and incubated at a temperature of −10° to 35° C. Following this, the reactant is added with the immobilized catalyst system in the absence of solvent while vigorously stirring. At this moment, the reaction is carried out preferably at a temperature of 0° to 35° C. under ordinary pressure. Particularly, care must be taken to control the temperature below 35° C. because higher temperature makes the reaction proceed too fast, resulting in degradation of optical purity.

High performance liquid chromatography can also be used about 3 hours after the reaction, to determine the termination of the reaction. Five hours after the reaction is usually enough to obtain the compound of Formula III with a yield of 85% or larger and an optical purity of 99% or more.

To identify (S)-2-aryl-1,3-propanediol monocarbamate as a pharmaceutically useful material, anticonvulsant activity assay of the novel compound of the present invention was executed through standard Maximal Electro-Shock (MES) test. To the end, 0.5 g (S)-2-phenyl-1,3-propanediol monocarbamate was suspended in 100 ml buffer solution at pH 7.4. The prepared suspension was administered into ten male CD-1 mice weighing about 20 to 25 g at a dose of 300 mg/kg. Oral administration through a syringe is preferred. At one hour after administration, the middle of the forehead of the mice was electrically shocked at 50 mA for 0.2 second by use of corneal electrode. Of the ten mice administered with the compound of the present invention, nine were not convulsed and acted as usual. Only one was convulsed to death.

A better understanding of the present invention may be obtained in light of following examples which are set forth to illustrate, and are not to be construed to limit, the present invention.

EXAMPLE I (S)-3-Acetoxy-2-(2-pyridyl) Propanol Carbamate 500 ml flask equipped with a thermometer was well dried and purged by flowing nitrogen gas into the inside thereof for 30 min. After the moisture and air present within the flask was replaced by nitrogen gas, 24.5 ml of 0.6M phosgene solution was placed in the purged flask, followed by the addition of 150 ml of toluene. The flask was maintained at −30° C. in a bath containing dry ice and acetone.

Separately, 2.0 g of (R)-3-acetoxy-2-(2-pyridyl)propanol and 4.7 g of antipyrine were placed in 100 ml flask well dried. To this, 70 ml chloroform was added.

To the phosgene/toluene solution maintained at −30° C., the (R)-3-acetoxy-2-(2-pyridyl) propanol solution was dropwise added with a double-ended needle. Following the completion of addition, thin layer chromatography was executed to know whether the starting materials were completely exhausted. Then, the reaction system was cooled to −70° C. and slowly added with 50 g of liquid ammonia. Reaction proceeded at −70° C. while stirring. Excess ammonia present in the reaction mixture was blown off by nitrogen gas at about 2 hours after the completion of reaction. While precipitate was filtered off and the solvents, toluene and chloroform, were removed by use of a rotary evaporator.

The resultant concentrated solution was subjected to column chromatography (mobile phase: ethyl acetate), giving forth (S)-3-acetoxy-2-(2-pyridyl) propanol carbamate: Yield 84.0%, purity 99.8%.

Physical Properties of (S)-3-acetoxy-2-(2-pyridyl) propanol carbamate: $[\alpha]=+45.3°$ (0.42 in acetone)

$^1$H-NMR (CDCl$_3$, 200 MHz), ppm ($\delta$): 1.99 (s, 3H), 3.52 (q, 1H), 4.43(m, 4H), 5.25 (br, 2H), 7.21(m, 2H), 7.68(m, 1H), 8.56(d, 1H)

EXAMPLE II

(S)-3-Acetoxy-2-(2-(3-chloro)pyridyl) Propanol Carbamate

The title compound was prepared in a similar manner to that of Example I, except that (R)-3-acetoxy-2-(2-(3-chloro) pyridyl) propanol, instead of (R)-3-acetoxy-2-(2-pyridyl) propanol, was used as a starting material: Yield 68.3%. Purity 98.5%.

$[\alpha]$=+53.1° (0.50 in acetone)

EXAMPLE III

(S)-3-Acetoxy-2-(2-(3-trifluoromethyl)pyridyl) Propanol Carbamate

The title compound was prepared in a similar manner to that of Example I, except that (R)-3-acetoxy-2-(2-(3-trifluoromethyl)pyridyl) propanol, instead of (R)-3-acetoxy-2-(2-pyridyl) propanol, was used as a starting material: Yield 63.2%. Purity 99.3%.

$[\alpha]$=+24.7° (0.50 in acetone)

EXAMPLE IV

(S)-3-Acetoxy-2-(2-(3-methyl)pyridyl) Propanol Carbamate

The title compound was prepared in a similar manner to that of Example I, except that (R)-3-acetoxy-2-(2-(3-methyl) pyridyl) propanol, instead of (R)-3-acetoxy-2-(2-pyridyl) propanol, was used as a starting material: Yield 76.8%. Purity 99.3%.

$[\alpha]$=+15.3° (0.50 in acetone)

EXAMPLE V

(S)-3-Acetoxy-2-(2-(3-thiomethyl)pyridyl) Propanol Carbamate

Except that (R)-3-acetoxy-2-(2-(3-thiomethyl)pyridyl) propanol, instead of (R)-3-acetoxy-2-(2-pyridyl) propanol, was used as a starting material, Example I was repeated to give the title compound: Yield 67.3%. Purity 99.1%.

$[\alpha]$=+37.8° (0.50 in acetone)

EXAMPLE VI

(S)-3-Acetoxy-2-(2-(4,6-dichloro)pyridyl) Propanol Carbamate

Except that (R)-3-acetoxy-2-(2-(4,6-dichloro)pyridyl) propanol, instead of (R)-3-acetoxy-2-(2-pyridyl) propanol, was used as a starting material, Example I was repeated to give the title compound: Yield 70.1%. Purity 99.2%.

$[\alpha]$=+48.3° (0.50 in acetone)

EXAMPLE VII

(S)-3-Acetoxy-2-(2-(4,6-dimethoxy)pyridyl) Propanol Carbamate

Except that (R)-3-acetoxy-2-(2-(4, 6-dimethoxy)pyridyl) propanol, instead of (R)-3-acetoxy-2-(2-pyridyl) propanol, was used as a starting material, Example I was repeated to give the title compound: Yield 72.9%. Purity 98.9%.

$[\alpha]$=+24.1° (0.50 in acetone)

EXAMPLE VIII

(S)-3-Acetoxy-2-phenylpropanol Carbamate

In a 250 mL flask equipped with a magnetic stirrer, 4.7 g of antipyrine (0.025 mole) and 1.94 g of (R)-3-acetoxy-2-phenylpropanol (0.01 mole) were placed. 80 mL of toluene and 20 mL of chloroform were poured into the flask. The resulting reaction solution was maintained at 0° C. while stirring.

To the solution, 14 mL of 0.6M phosgene was added at 0° C. while stirring. White precipitate was evidence that the reaction was making progress. After five hours, the reaction was terminated, and the reaction mixture was subjected to filtration.

The filtrate was maintained at 0° C. and ammonia gas was flowed into the flask for 30 minutes. After being stirred for 30 minutes, the mixture was filtered to remove precipitate. The solvents used were distilled off in vacuo.

Isolation by column chromatography (using ethyl acetate and n-hexane (1:1) as the mobile phase) gave (S)-3-acetoxy-2-phenylpropanol carbamate: Yield 87.2%. Purity 99.2%.

Physical properties of (S)-3-acetoxy-2-phenylpropanol carbamate: $[\alpha]$=+2.5° (0.03 in $CHCl_3$)

$^1$H-NMR ($CDCl_3$, 200 MHz), ppm ($\delta$): 1.99(s, 3H), 3.21–3.37(m, 1H), 4.21–4.38(m, 4H), 5.14(b, 2H), 7.21–7.30(m, 5H)

EXAMPLE IX

(S)-3-Acetoxy-2-(o-chlorophenyl)propanol Carbamate

The title compound was synthesized in a similar manner to that of Example VIII, except that (R)-3-acetoxy-2-(o-chlorophenyl) propanol, instead of (R)-3-acetoxy-2-phenyl propanol, was used as a starting material. Yield 63.1%. Purity 99.3%.

$[\alpha]$=+13.7° (0.50 in methanol)

EXAMPLE X

(S)-3-Acetoxy-2-(o-trifluoromethylphenyl)propanol Carbamate

The title compound was synthesized in a similar manner to that of Example VIII, except that (R)-3-acetoxy-2-(o-trifluoromethyl phenyl) propanol, instead of (R)-3-acetoxy-2-phenyl propanol, was used as a starting material. Yield 63.1%. Purity 99.6%.

$[\alpha]$=+32.5° (0.50 in methanol)

EXAMPLE XI

(S)-3-Acetoxy-2-(o-methylphenyl)propanol Carbamate

The title compound was synthesized in a similar manner to that of Example VIII, except that (R)-3-acetoxy-2-(o-methylphenyl) propanol, instead of (R)-3-acetoxy-2-phenyl propanol, was used as a starting material. Yield 78.7%. Purity 98.5%.

$[\alpha]$=+8.3° (0.50 in methanol)

EXAMPLE XII

(S)-3-Acetoxy-2-(o-thiomethylphenyl) Propanol Carbamate

The title compound was synthesized in a similar manner to that of Example VIII, except that (R)-3-acetoxy-2-(o-thiomethylphenyl) propanol, instead of (R)-3-acetoxy-2-phenyl propanol, was used as a starting material. Yield 60.3%. Purity 99.4%.

[α]=+21.9° (0.50 in methanol)

EXAMPLE XIII

(S)-3-Acetoxy-2-(2,4-dicholrophenyl) Propanol Carbamate

Except that (R)-3-acetoxy-2-(2,4-dichlorophenyl) propanol, instead of (R)-3-acetoxy-2-phenyl propanol, was used as a starting material, Example VIII was repeated to give the title compound. Yield 67.5%. Purity 99.7%.

[α]=+21.7° (0.50 in methanol)

EXAMPLE XIV

(S)-3-Acetoxy-2-(2,4-dimethoxyphenyl) Propanol Carbamate

Except that (R)-3-acetoxy-2-(2,4-dimethoxyphenyl) propanol, instead of (R)-3-acetoxy-2-phenyl propanol, was used as a starting material, Example VIII was repeated to give the title compound. Yield 63.0%. Purity 99.1%.

[α]=+12.4° (0.50 in methanol)

EXAMPLE XV

(S)-2-(2-pyridyl)-1,3-propanediol Monocarbamate

In a well dried 250 mL flask, 1.0 g of (S)-3-acetoxy-2-(2-pyridyl)propanol carbamate obtained in Example I was placed with 200 mL of 0.05M phosphate buffer solution (pH 7) and 1.1 g of PLE-A and then, the resulting mixture was vigorously stirred at a room temperature for five hours. Subsequently, 200 mL of ethyl acetate was added to the well stirred mixture, for solvent extraction. This extraction was repeated three times.

The ethyl acetate solution obtained was dried over anhydrous magnesium sulfate. A rotary evaporator was used to remove extra ethyl acetate. Isolation by column chromatography gave (S)-2-(2-pyridyl)-1,3-propanediol monocarbamate: Yield 60.0%. Purity 99.5%.

Physical properties of (S)-2-(2-pyridyl)-1,3-propanediol carbamate: [α]=+24.1° (0.30 in acetone)

$^1$H-NMR (CDCl$_3$, 200 MHz), ppm (δ): 3.21(s, 1H), 3.66(m, 2H), 4.30(m,2H), 6.43(br, 2H), 7.31(m, 2H), 7.76 (m, 1H), 8.53(d, 1H)

EXAMPLE XVI

(S)-2-(2-(3-Chloro)pyridyl)-1,3-propanediol Monocarbamate

Except for using (S)-3-acetoxy-2-(2-(3-cholro)pyridyl) propanol carbamate, instead of (S)-3-acetoxy-2-(2-pyridyl) propanol carbamate, as a starting material, Example XV was repeated to give the title compound: Yield 57.3%. Purity 99.8%.

[α]=+27.8° (0.50 in methanol)

EXAMPLE XVII

(S)-2-(2-(3-Trifluoromethyl)pyridyl)-1,3-propanediol Monocarbamate

Except for using (S)-3-acetoxy-2--(2-(3-trifluoromethyl) pyridyl)propanol carbamate, instead of (S)-3-acetoxy-2-(2-pyridyl)propanol carbamate, as a starting material, Example XV was repeated to give the title compound: Yield 63.2%. Purity 99.3%.

[α]=+3.5° (0.50 in methanol)

EXAMPLE XVIII

(S)-2-(2-(3-Methyl)pyridyl)-1,3-propanediol Monocarbamate

Except for using (S)-3-acetoxy-2-(2-(3-methyl)pyridyl) propanol carbamate, instead of (S)-3-acetoxy-2-(2-pyridyl) propanol carbamate, as a starting material, Example XV was repeated to give the title compound: Yield 72.8%. Purity 98.7%.

[α]=+8.7° (0.50 in methanol)

EXAMPLE XIX

(S)-2-(2-(3-Thiomethyl)pyridyl)-1,3-propanediol Monocarbamate

Except for using (S)-3-acetoxy-2-(2-(3-thiomethyl) pyridyl)propanol carbamate, instead of (S)-3-acetoxy-2-(2-pyridyl)propanol carbamate, as a starting material, Example XV was repeated to give the title compound: Yield 67.5%. Purity 99.5%.

[α]=+20.4° (0.50 in methanol)

EXAMPLE XX

(S)-2-(2-(4,6-dichloro)pyridyl)-1,3-propanediol Monocarbamate

The title compound was synthesized in a similar manner to that of Example XV, except that (S)-3-acetoxy-2-(2-(4,6-dichloro)pyridyl)propanol carbamate, instead of (S)-3-acetoxy-2-(2-pyridyl)propanol carbamate, was used as a starting material. Yield 60.5%. Purity 99.5%.

[α]=+33.1° (0.50 in methanol)

EXAMPLE XXI

(S)-2-(2-(4,6-dimethoxy)pyridyl)-1,3-propanediol Monocarbamate

The title compound was synthesized in a similar manner to that of Example XV, except that (S)-3-acetoxy-2-(2-(4,6-dimethoxy)pyridyl)propanol carbamate, instead of (S)-3-acetoxy-2-(2-pyridyl) propanol carbamate, was used as a starting material. Yield 70.4%. Purity 99.5%.

[α]=+11.8° (0.50 in methanol)

EXAMPLE XXII

(S)-2-Phenyl-1,3-propanediol Monocarbamate

In a 500 mL flask equipped with a magnetic stirrer, 2.37 g of (S)-3-acetoxy-2-phenylpropanol carbamate (0.01 mole) obtained in Example VIII was placed and 200 mL of phosphate buffer solution (0.014 mole, pH 7) and 1.2 g of PLE-A were added. The reaction mixture was stirred at room temperature.

When the conversion rate of (S)-3-acetoxy-2-phenylpropanol carbamate reached 90%, which was detected by HPLC, the reaction was stopped and the resulting mixture was filtered. The filtrate was extracted three times with ethyl acetate, to isolate an organic layer of which the extra solvent was then distilled off by a rotary evaporator. Isolation by column chromatography using a mixture of ethyl acetate and n-hexane (1:1) as the mobile phase gave (S)-2-phenyl-1,3-propanediol monocarbamate: Yield 70.1%. Purity 99.7%.

Physical properties of (S)-2-phenyl-1,3-propanediol monocarbamate: [α]=+1.8° (0.03 in ethanol)

¹H-NMR (CDCl₃, 200 MHz), ppm (6): 2.49–2.63(m, 1H), 2.95–3.21(m, 1H), 3.75–3.88(m, 2H), 4.37(d, 2H), 4.91(b, 2H), 7.21–7.36(m, 5H)

EXAMPLE XXIII (S)-2-(o-Chlorophenyl)-1,3-propanediol Monocarbamate

The title compound was synthesized in a similar manner to that of Example XXII, except that (S)-3-acetoxy-2-(o-cholrophenyl)propanol carbamate, instead of (S)-3-acetoxy-2-phenylpropanol carbamate, was used as a starting material. Yield 76.3%. Purity 99.3%.

[α]=+8.7° (0.50 in methanol)

EXAMPLE XXIV (S)-2-(o-Trifluoromethylphenyl)-1,3-propanediol Monocarbamate

The title compound was synthesized in a similar manner to that of Example XXII, except that (S)-3-acetoxy-2-(o-trifluoromethylphenyl)propanol carbamate, instead of (S)-3-acetoxy-2-phenylpropanol carbamate, was used as a starting material. Yield 63.5%. Purity 99.4%.

[α]=+21.3° (0.50 in methanol)

EXAMPLE XXV (S)-2-(o-methylphenyl)-1,3-propanediol Monocarbamate

The title compound was synthesized in a similar manner to that of Example XXII, except that (S)-3-acetoxy-2-(o-methylphenyl)propanol carbamate, instead of (S)-3-acetoxy-2-phenylpropanol carbamate, was used as a starting material. Yield 78.3%. Purity 99.0%.

[α]=+5.2° (0.50 in methanol)

EXAMPLE XXVI (S)-2-(o-Thiomethylphenyl)-1,3-propanediol Monocarbamate

The title compound was synthesized in a similar manner to that of Example XXII, except that (S)-3-acetoxy-2-(o-thiomethylphenyl)propanol carbamate, instead of (S)-3-acetoxy-2-phenylpropanol carbamate, was used as a starting material. Yield 75.7%. Purity 98.7%.

[α]=+18.2° (0.50 in methanol)

EXAMPLE XXVII (S)-2-(2,4-Dichlorophenyl)-1,3-propanediol Monocarbamate

The title compound was synthesized in a similar manner to that of Example XXII, except that (S)-3-acetoxy-2-(2,4-dichlorophenyl)propanol carbamate, instead of (S)-3-acetoxy-2-phenylpropanol carbamate, was used as a starting material. Yield 78.9%. Purity 99.7%.

[α]=+18.0° (0.50 in methanol)

EXAMPLE XXVIII (S)-2-(2,4-dimethoxyphenyl)-1,3-propanediol Monocarbamate

The title compound was synthesized in a similar manner to that of Example XXII, except that (S)-3-acetoxy-2-(2,4-dimethoxyphenyl)propanol carbamate, instead of (S)-3-acetoxy-2-phenylpropanol carbamate, was used as a starting material. Yield 65.3%. Purity 99.2%.

[α]=+25.1° (0.50 in methanol)

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. (S)-2-Aryl-1,3-propanediol monocarbamate, represented by the following Formula I:

[I]

wherein, R is

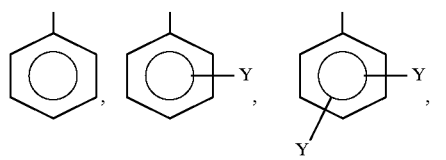

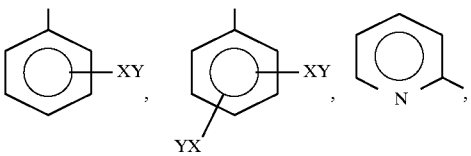

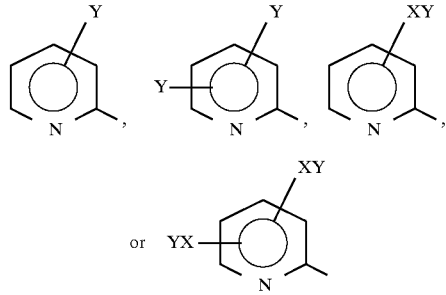

wherein X is an oxygen atom or a sulfur atom; and Y represents a halogen element, trifluoromethyl, or a lower alkyl group containing one to three carbon atoms.

2. (S)-3-Acetoxy-2-arylpropanol carbamate, represented by the following Formula II:

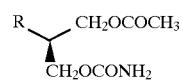

[II]

wherein, R is

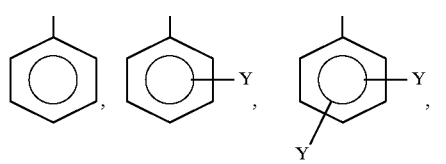

-continued

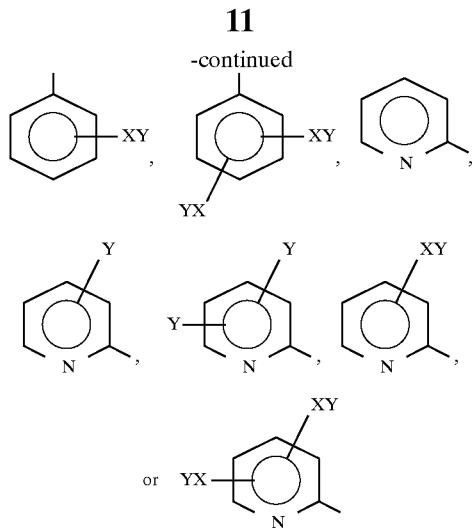

wherein X is an oxygen atom or a sulfur atom; and Y represents a halogen element, trifluoromethyl, or a lower alkyl group containing one to three carbon atoms.

3. A process for preparing (S)-3-acetoxy-2-arylpropanol carbamate, represented by the following Formula II:

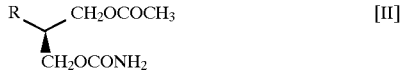

wherein, R is

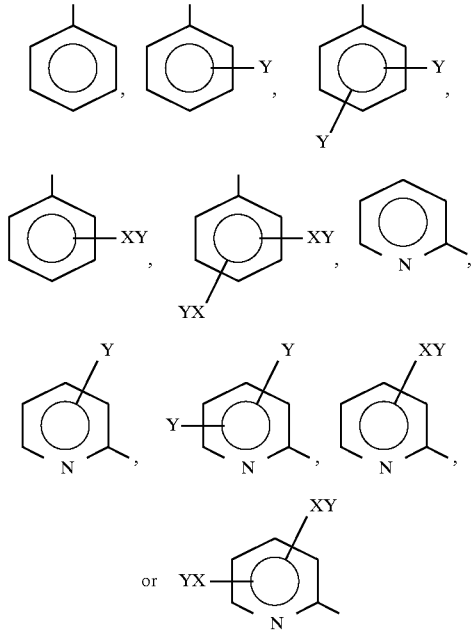

wherein X is an oxygen atom or a sulfur atom; and Y represents a halogen element, trifluoromethyl, or a lower alkyl group containing one to three carbon atoms, in which (R)-3-acetoxy-2-aryl-propanol, represented by the following Formula III:

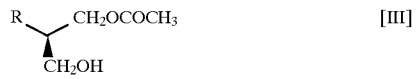

wherein R is as defined above, is reacted with phosgene in the presence of amine base in a solvent mixture of aromatic hydrocarbon and halogenohydrocarbon and then with ammonia, whereby a high optical purity can be obtained within a short time.

4. The process in accordance with claim 3, wherein said solvent mixture comprises an aromatic hydrocarbon selected from the group consisting of benzene, toluene and xylene and a halogenohydrocarbon selected from the group consisting of chloroform, dichloromethane, 1,2-dichloroethane, and trichloroethane.

5. The process in accordance with claim 4, wherein said solvent mixture comprises toluene and dichloromethane.

6. The process in accordance with claim 3, wherein said amine base is selected from the group consisting of antipyrine, diisopropylethyl amine, diethyl amine, triethyl amine and pyridine.

7. The process in accordance with claim 3, wherein reaction temperature is −30° to 0° C. for phosgen and −70° C. to 0° C. for ammonia.

8. The process in accordance with claim 3, wherein said ammonia condensed to liquid and is used in an excess of 10 to 100 equivalents.

9. A process for preparing (S)-2-aryl-1,3-propanediol monocarbamate, represented by the following Formula I:

wherein, R is

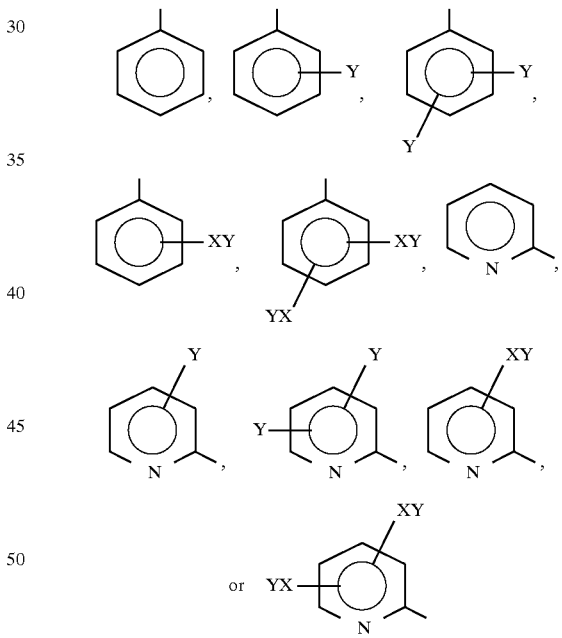

wherein X is an oxygen atom or a sulfur atom; and Y represents a halogen element, trifluoromethyl, or a lower alkyl group containing one to three carbon atoms, in which (S)-3-acetoxy-2-aryl-propanol carbamate, represented by the following Formula II:

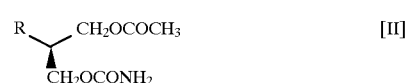

wherein R is as defined above, is dissolved in a phosphate buffer solution and added with hydrolase with vigorous stirring, whereby a high optical purity can be obtained within a short time.

10. The process in accordance with claim 9, wherein the reaction is carried out at a temperature of 0° to 35° C. under ordinary pressure.

11. The process in accordance with claim 9, wherein said phosphate buffer solution has a pH of 6 to 9 and a concentration of 0.01 to 0.1M.

12. The process in accordance with claim 9, wherein said hydrolase is selected from the group consisting of a lipase extracted from pig's pancreas, Candida lipase, Aspagillus lipase, Pseudomonas lipase and an esterase extracted from pig's liver.

13. The process in accordance with claim 12, wherein said hydrolase is an esterase extracted from pig's liver.

14. A method for treating central nervous system disorders, which comprises administering to a mammal suffering from a central nervous system disorder an effective amount of a compound of the Formula as defined in claim 1 as an active ingredient.

* * * * *